United States Patent
Nagai et al.

(10) Patent No.: US 10,578,544 B2
(45) Date of Patent: Mar. 3, 2020

(54) FLOW CELL

(71) Applicant: Shimadzu Corporation, Kyoto (JP)

(72) Inventors: Yusuke Nagai, Kyoto (JP); Masato Watanabe, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/318,789

(22) PCT Filed: Aug. 25, 2016

(86) PCT No.: PCT/JP2016/074831
§ 371 (c)(1),
(2) Date: Jan. 18, 2019

(87) PCT Pub. No.: WO2018/037536
PCT Pub. Date: Mar. 1, 2018

(65) Prior Publication Data
US 2019/0187045 A1 Jun. 20, 2019

(51) Int. Cl.
*G01N 21/01* (2006.01)
*G01N 21/05* (2006.01)
*G01N 30/74* (2006.01)
*G01N 21/03* (2006.01)

(52) U.S. Cl.
CPC .............. *G01N 21/01* (2013.01); *G01N 21/05* (2013.01); *G01N 30/74* (2013.01); *G01N 2021/0378* (2013.01); *G01N 2021/0392* (2013.01); *G01N 2030/746* (2013.01); *G01N 2201/0639* (2013.01)

(58) Field of Classification Search
CPC ...................................................... G01N 21/01

USPC .......................................................... 356/246
See application file for complete search history.

(56) References Cited

U.S. PATENT DOCUMENTS

| 5,408,313 A | * | 4/1995 | Ponstingl | ............ G01N 21/8507 356/246 |
| 6,127,690 A | * | 10/2000 | Kitaoka | .................. G01N 30/74 250/573 |

(Continued)

FOREIGN PATENT DOCUMENTS

| JP | 2012-522253 A | 9/2012 |
| JP | 2014-055784 A | 3/2014 |
| WO | 2013/190747 A1 | 12/2013 |

OTHER PUBLICATIONS

Translation of International Search Report and Written Opinion dated Nov. 22, 2016 of corresponding application No. PCT/JP2016/074831; 5 pgs.

(Continued)

*Primary Examiner* — Tarifur R Chowdhury
*Assistant Examiner* — Omar H Nixon
(74) *Attorney, Agent, or Firm* — Maier & Maier, PLLC

(57) ABSTRACT

A flow cell includes a housing, a window member, and a pressing member. The housing includes a cell channel in which a sample flows through, has, on at least one end side of the cell channel, an opening communicating with the cell channel, and has a flat surface at an edge of the opening. The window member has a lens portion at a central portion and a peripheral edge portion whose one surface and the other surface are flat. In the window member, one surface of the peripheral edge portion is provided facing the flat surface of the housing so as to seal the opening.

4 Claims, 5 Drawing Sheets

(56) References Cited

U.S. PATENT DOCUMENTS

| | | | |
|---|---|---|---|
| 2005/0036214 A1* | 2/2005 | Jewers | G02B 5/005 |
| | | | 359/738 |
| 2010/0265492 A1 | 10/2010 | Schroeder | |
| 2012/0140221 A1* | 6/2012 | Salton | G01N 15/0205 |
| | | | 356/337 |
| 2012/0285872 A1 | 11/2012 | Shreve et al. | |

OTHER PUBLICATIONS

Extended European Search Report dated Nov. 28, 2019, in corresponding European application No. 19175321.9; 7 pages.

* cited by examiner

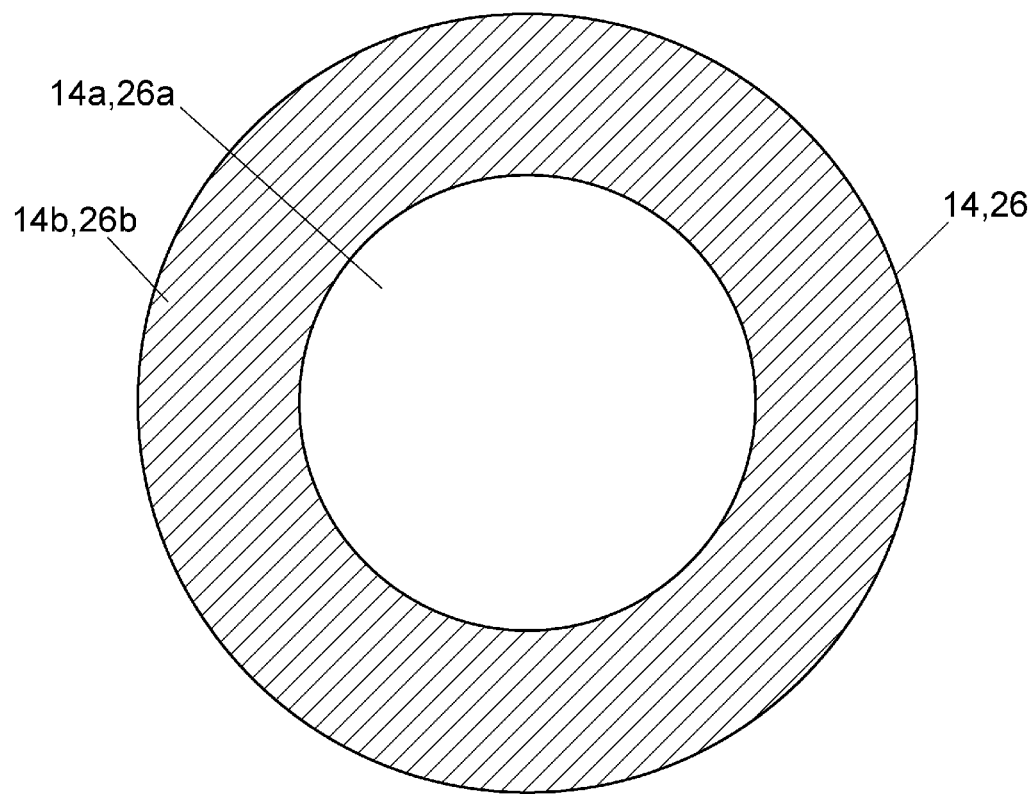

(A)

(B)

(C)

FLOW CELL

FIELD

The present invention relates to a flow cell used for a detector of an analyzer such as a liquid chromatograph.

BACKGROUND

A method of irradiating a sample with light and analyzing the sample using the transmitted light, the reflected light, or the scattered light is widely known as an absorbance measurement method or the like. In these measurement methods, a flow cell including a cell channel serving as a flow path through which a sample flows is used. A transparent window member used for taking light into the cell channel is attached to the flow cell. Here, "transparent" means that the transmittance is high (at least 80% or more) with respect to the wavelength of light used for analysis. Examples of the transparent window member include a flat window formed of synthetic quartz.

In order to efficiently irradiate a sample, flowing through the cell channel in the flow cell, with light, a lens such as a hemispherical lens or a ball lens may be used. In this case, although the lens may be disposed outside a window portion of the flow cell, the lens is used as the window member of the flow cell in order to, for example, reduce the number of parts (see Patent Document 1).

Patent Document 1: Japanese Patent Laid-open Publication No. 2014-55784

Patent Document 2: Japanese Unexamined Patent Publication No. 2012-522253

SUMMARY

In a flow cell using a lens as a window member, in order to fix the lens to a housing of the flow cell, a method is generally adopted in which a resin packing having a certain degree of elasticity is disposed on the front side (cell channel side) and the back side (the opposite side of the cell channel side) of the lens, and the back surface of the lens is pressed toward the cell channel by a screw type fixing member through the resin packing, whereby the lens is stably fixed at an end of the cell channel to prevent liquid leakage from the cell channel.

However, since one surface of the lens has a curvature, contact between a lens curved surface and the resin packing becomes line contact, and fixation of the lens tends to become unstable. If the fixing member is excessively tightened in order to stabilize the fixation of the lens, there is also a problem that the resin packing flows (is plastically deformed).

In particular, in order to hold the lens in a high voltage environment, a method is also provided in which a resin packing on the back side of the lens is an O-ring, and the lens is pressed toward the cell channel through the O-ring (see Patent Document 2). Although it is generally said that a risk of flow is reduced by using the O-ring, there is no change in holding by line contact.

Although the lens and the resin packing on the back side of the lens are preferably in surface contact with each other, it is difficult to produce a resin packing having the same curved surface as the curved surface of the lens, and it is a limit that the lens is held by a plurality of line contacts.

It is therefore an object of the present invention to provide a flow cell capable of stably fixing a window member having a lens function.

A flow cell according to the present invention comprising; a housing including a cell channel in which a sample flows through, wherein the housing comprises an opening which is communicating with the cell channel and is provided on at least one end side of the cell channel, and a flat surface at an edge of the opening; a window member comprising a lens portion at a central portion, wherein one surface and the other surface of a peripheral edge portion of the window member are flat, and one surface of the peripheral edge portion is provided facing the flat surface of the housing so as to seal the opening; and a pressing member provided opposite to the cell channel with the window member interposed therebetween, wherein the pressing member has in the central portion a hole through which light passes, and is in surface contact with the other surface of the peripheral edge portion of the window member to press the window member toward the cell channel.

An example of the lens portion of the window member is one having a convex lens on a surface opposite to the cell channel.

In the above case, it is preferable that the convex lens has a lateral surface which is perpendicular to a surface of the peripheral edge portion or forms an angle larger than 90 degrees with respect to the surface of the peripheral edge portion. Thus, the window member is easily held with tweezers or the like. In this case, the lateral surface of the convex lens may be a straight flat surface or a curved flat surface from the base end side to the tip end side of the lens.

It is preferable that the peripheral edge portion of the window member has lower light transmittance than the lens portion. Thus, it becomes difficult for light to pass through the portion other than the lens portion of the window member, and the influence of scattered light or the like can be reduced. Such a structure can be realized by making surface roughness of the peripheral edge portion greater than the lens portion.

In the flow cell of the present invention, the window member has the lens portion at the central portion and the peripheral edge portion whose one surface and the other surface are flat, one surface of the peripheral edge portion is provided facing the flat surface of the housing so as to seal the opening of the housing, and the pressing member is provided opposite to the cell channel with the window member interposed therebetween and is in surface contact with the other surface of the peripheral edge portion of the window member to press the window member toward the cell channel, so that the window member can be stably fixed by the pressing member.

BRIEF DESCRIPTION OF THE DRAWINGS

FIG. 3B is a plan view thereof.

FIG. 3B is a plan view of the window member.

DETAILED DESCRIPTION

Hereinafter, an embodiment of a flow cell according to the present invention will be described with reference to the drawings.

Figure 1:
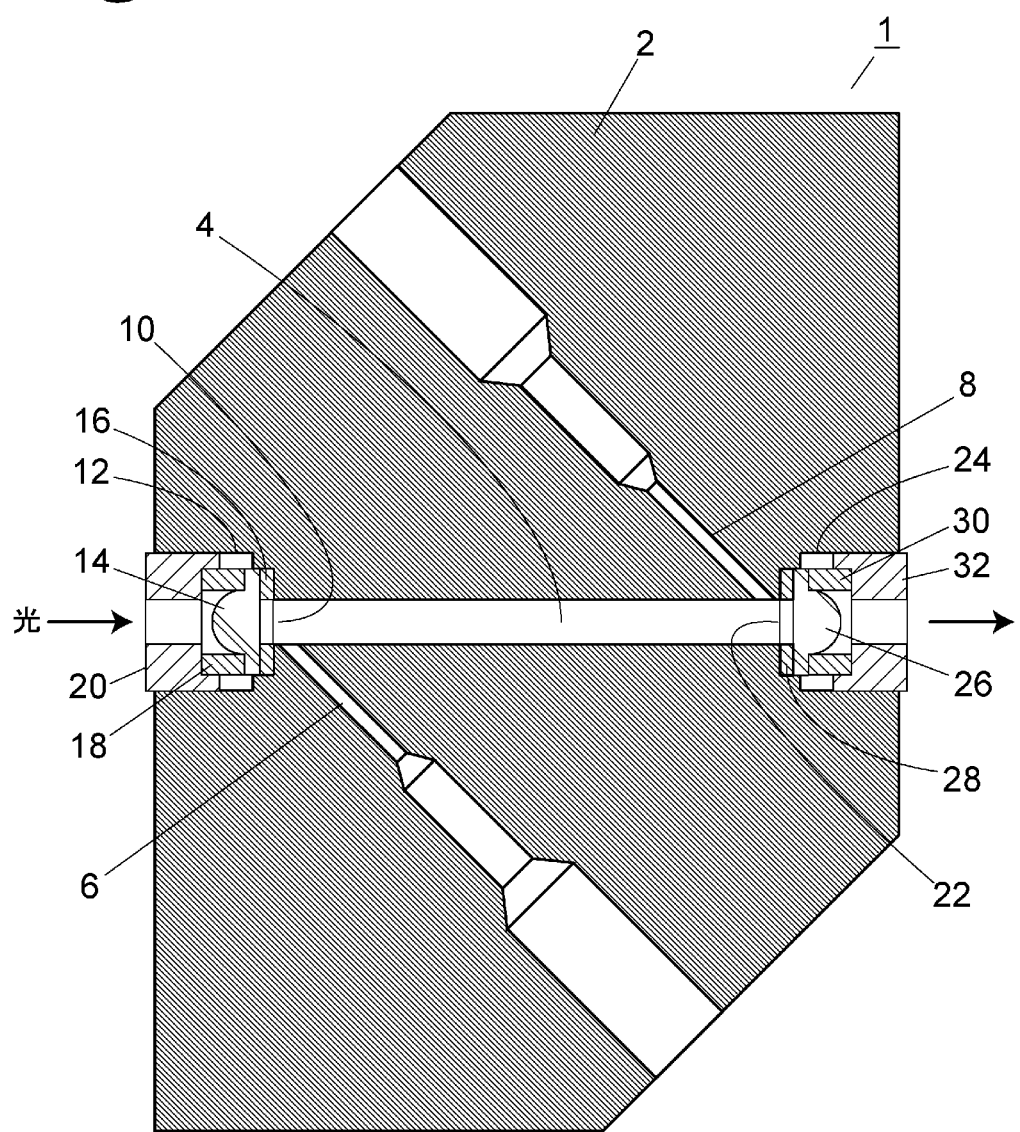
FIG. 1 is a cross-sectional view showing one embodiment of a flow cell.

As shown in FIG. 1, in a flow cell 1 of this embodiment, a housing 2 includes a cell channel 4 in which a sample flows through, an inlet flow path 6 through which a liquid is introduced from one end side (the left side in the drawing) of the cell channel 4, and an outlet flow path 8 through which the liquid is discharged from the other end side (the right side in the drawing) of the cell channel 4.

The housing 2 is provided with a window member attachment portion 12 for attaching a window member 14 to one end portion of the cell channel 4. The window member attachment portion 12 is a recess dug down from a surface of the housing 2 toward one end portion of the cell channel 4 and has an inner diameter larger than the inner diameter of the cell channel 4. An opening 10 communicating with one end of the cell channel 4 is provided at a bottom of the window member attachment portion 12, and the window member 14 is disposed so as to seal the opening 10. A circular dent is provided around the opening 10. A ring-shaped resin packing 16 and a portion of the window member 14 having a lens portion 14a (see FIG. 2) at the central portion are fitted in the dent around the opening 10.

Figure 2:
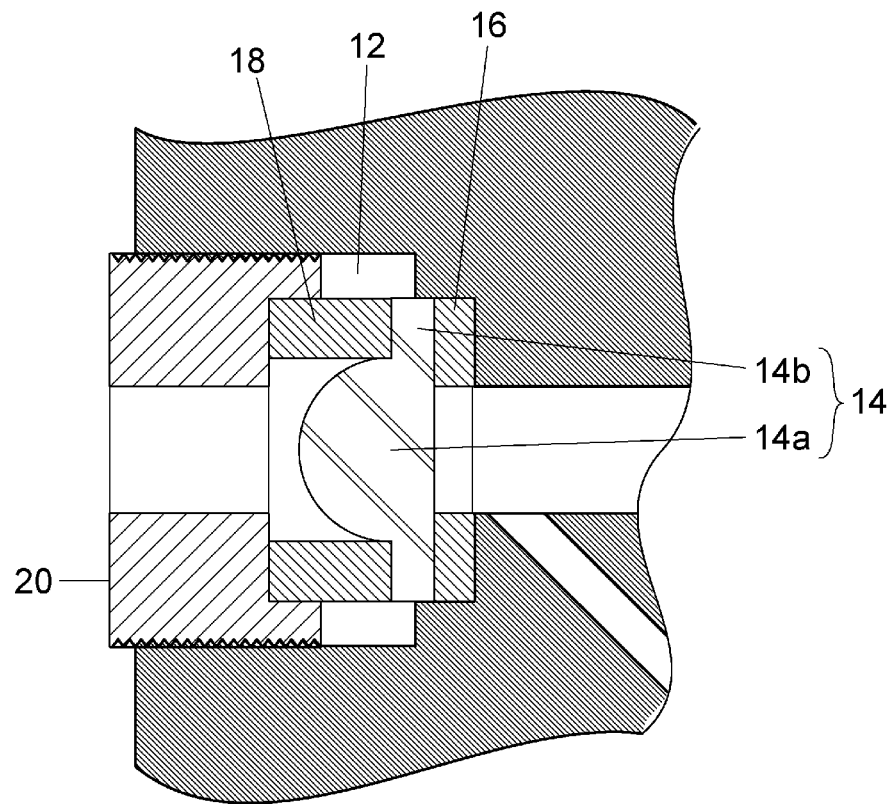
FIG. 2 is a cross-sectional view for explaining in more detail an opening of a cell channel end portion of the embodiment.

As shown in FIG. 2, both surfaces (the surface on the cell channel 4 side and the opposite surface) of a peripheral edge portion 14b of the window member 14 are flat surfaces, and the peripheral edge portion 14b is pressed toward the resin packing 16 by a fixing member 20 through a ring-shaped resin packing 18. Screws screwed together are provided on an inner peripheral surface of the window member attachment portion 12 and an outer peripheral surface of the fixing member 20. The fixing member 20 moved along a center axis of the cell channel 4 by rotating the fixing member 20 about the center axis of the cell channel 4 as a rotation center. That is, by rotating the fixing member 20, the strength of the force pressing the peripheral edge portion 14b of the window member 14 toward the resin packing 16 is adjusted through the resin packing 18.

Returning to FIG. 1, the same structure as the one end side of the cell channel 4 is provided also on the other end side (the left side in the drawing) of the cell channel 4 of the housing 2. That is, on the other end side of the cell channel 4 of the housing 2, a window member attachment portion 24 for attaching a window member 26 to the other end portion of the cell channel 4 is provided. The window member attachment portion 26 is a recess dug down from the surface of the housing 2 toward the other end portion of the cell channel 4 and has an inner diameter larger than the inner diameter of the cell channel 4. An opening 22 communicating with one end of the cell channel 4 is provided at a bottom of the window member attachment portion 24, and the window member 26 is disposed so as to seal the opening 22. A circular dent is provided around the opening 22. A ring-shaped resin packing 28 and a portion of the window member 26 having a lens portion at the central portion are fitted in the dent around the opening 22.

The window member 26 has the same structure as the window member 14, and a flat peripheral edge portion of the window member 26 is pressed toward the resin packing 28 by a fixing member 32 through a ring-shaped resin packing 30. Screws screwed together are provided on an inner peripheral surface of the window member attachment portion 24 and an outer peripheral surface of the fixing member 32. The fixing member 32 moved along the center axis direction of the cell channel 4 by rotating the fixing member 32 about the center axis of the cell channel 4 as a rotation center. That is, by rotating the fixing member 32, the strength of the force pressing the peripheral edge portion of the window member 26 toward the resin packing 28 is adjusted through the resin packing 30.

A pair of the resin packing 18 and the fixing member 20 and a pair of the resin packing 30 and the fixing member 32 each constitute a pressing member for pressing the peripheral edge portion of the window member 14 or 26 toward the cell channel 4. The resin packings 18 and 30 are in surface contact with the peripheral edge portions of the window members 14 and 26, respectively, and stably press the window members 14 and 26 toward the resin packings 16 and 28, respectively.

Here, the window members 14 and 26 are formed of a material transparent to the wavelength of light used for measurement, such as fused quartz, quartz, hard glass, or an engineering plastic. The material that is "transparent" to the wavelength of light used for measurement means that the transmittance of the wavelength of light to be used is 80% or more. The same meaning also applies to the term "transparent" below.

Examples of the material of the resin packings 16, 18, 28 and 30 include materials having corrosion resistance, chemical resistance, and elasticity, and are hard to deform due to inertia, such as PCTFE (polychlorotrifluoroethylene) and PEEK (polyetherether Ketone).

Preferred embodiments of the window members 14 and 26 will be described with reference to FIGS. 3A and 3B.

In this example, the lens portions 14a and 26a at the central portions of the window members 14 and 26 each have a convex curved surface on one surface side, and a lateral surface of the convex portion is orthogonal to the flat peripheral edge portion 14b or 26b therearound. While a surface (curved surface) having a curvature of the lens portion 14a or 26a has a surface roughness of 0.2 μm or less, a lateral surface 14c or 26c of the lens portion 14a or 26a and a surface on the convex surface side (the upper side in the drawing) of the peripheral edge portion 14b or 26b have a surface roughness of 12.8 μm or more and are in a frosted glass state.

Since the surfaces of the peripheral edge portions 14b and 26b are in the frosted glass state, the light transmittance of the peripheral edge portions 14b and 26b is significantly inferior to the light transmittance of the curved surfaces of the lens portions 14a and 26a. This prevents light from entering from portions other than the lens portions 14a and 26a. Since the lateral surfaces 14c and 26c of the lens portions 14a and 26a have a surface roughness of 12.8 μm or more, the friction resistance of the lateral surfaces 14c and 26c increases, so that the window member 14 can be easily held with tweezers or the like.

In this embodiment, although the lateral surfaces 14c and 26c of the lens portions 14a and 26a are orthogonal to the respective peripheral edge portions 14b and 26b, an angle formed by the lateral surface 14c or 26c and the peripheral edge portion 14b or 26b may be larger than 90 degrees. It is not necessary that the lateral surfaces 14c and 26c are straight from the base end sides to the tip end sides of the lens portions 14a and 26a, and they may be curved.

Figure 4:
FIG. 4 is a process cross-sectional view showing an example of a production process of the window member.
Figure 4:
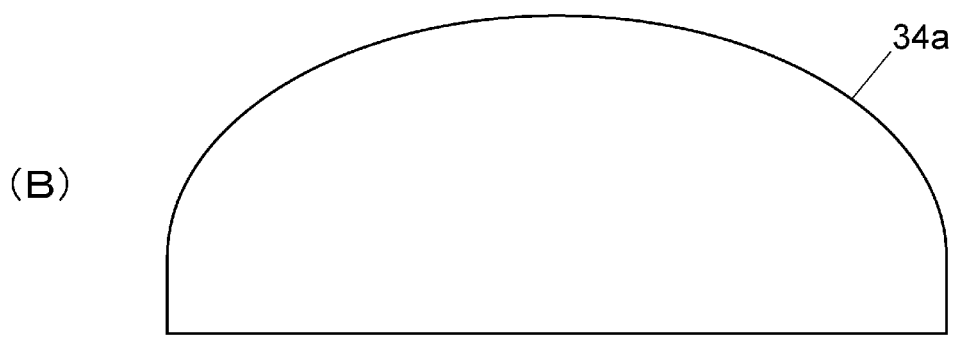
Figure 4:
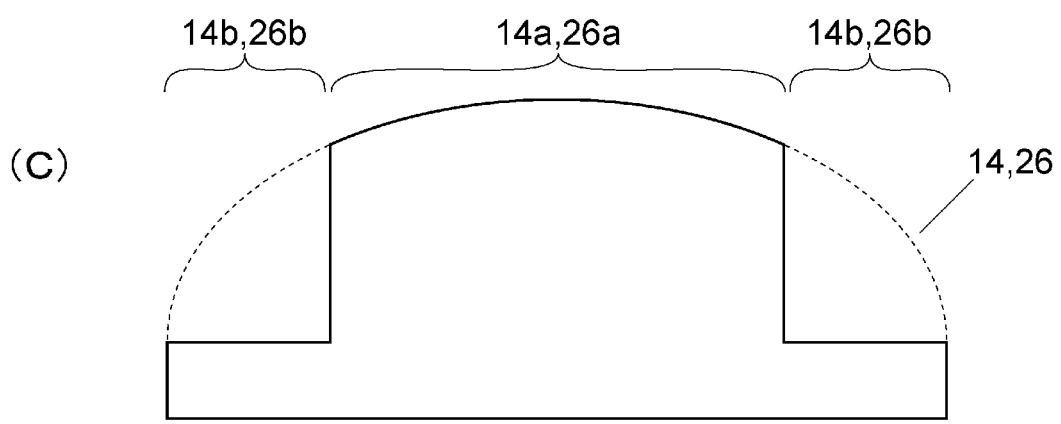

The window members 14 and 26 thus configured can be produced by shaving from one block 34, as shown in FIG. 4. Specifically, the block 34 formed of a material transparent to the wavelength of light used for measurement is prepared (see FIG. 4(A)) and cut in such a way that the entire one surface becomes a curved surface (see FIG. 4(B)). Thereafter, cutting is performed using rotation so that a peripheral edge portion of a curved surface of a block 34a whose one surface is curved becomes a flat surface, whereby the peripheral edge portions 14b and 26b whose both surfaces are flat are formed around the lens portions 14a and 26a having a curved surface. The surface processing of the curved surfaces of the lens portions 14a and 26a may be performed before or after the process of forming the peripheral edge portions 14b and 26b.

Figure 3A:
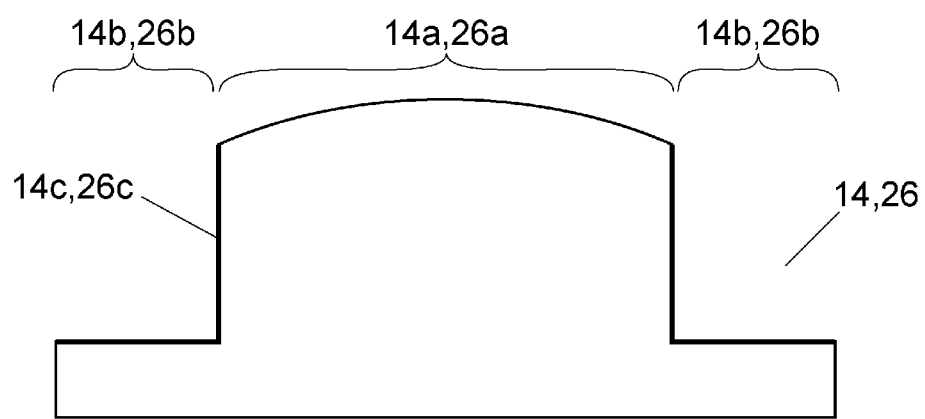
FIG. 3A is a cross-sectional view showing an example of the window member of the embodiment.

In the window members 14 and 26, as shown in FIGS. 3A and 3B, it is not always necessary that the lens portions 14a and 26a have lateral surfaces orthogonal to the surfaces of the peripheral edge portions 14b and 26b.

Figure 5:
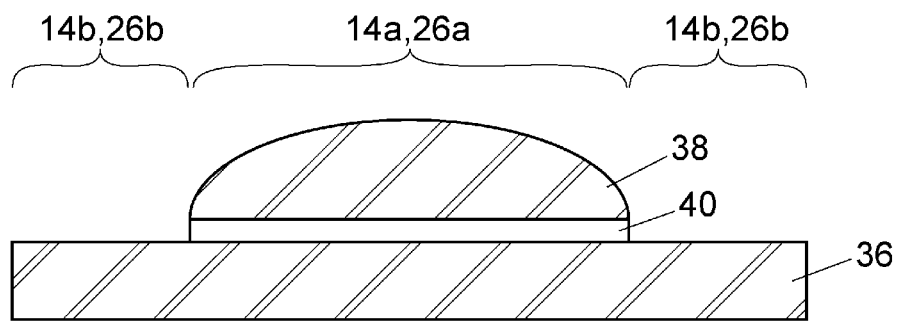
FIG. 5 is a cross-sectional view showing another example of the window member.
Figure 6:
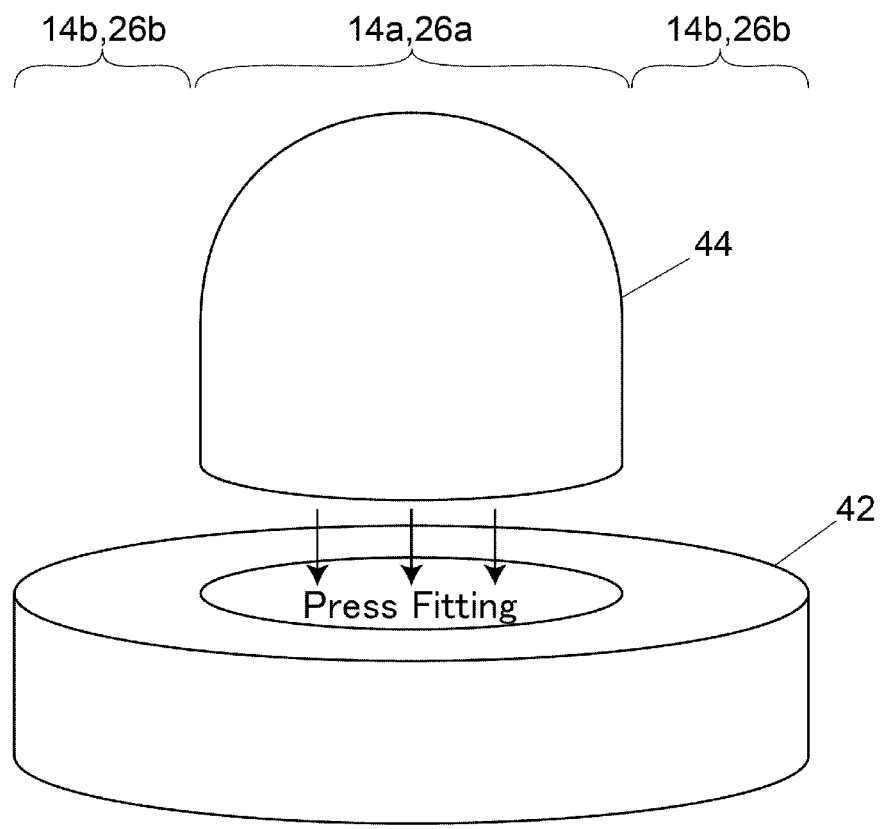
FIG. 6 is an exploded cross-sectional view showing still another example of the window member.

In the window members 14 and 26, as shown in FIG. 5, a substantially hemispherical lens member 38 may be adhered to one surface of a transparent flat plate 36 with a matching oil 40, or the flat plate 36 and the lens member 38 may be joined by melt bonding or the like in place of adhesion.

The window members 14 and 26 may be configured by press fitting a transparent lens member 44 whose one side (the upper side in the drawing) has a substantially hemispherical shape and the other side (the lower side in the drawing) has a cylindrical shape into a through hole provided in the center of a ring-shaped base material 42. In this case, the base material 42 constitutes the peripheral edge portions 14b and 26b of the window members 14 and 26. However, since there is no need to transmit light at this portion, the material of the base material 42 may not be transparent. An example of the material of the base material 42 is polyimide.

In the embodiment described above, the lens portions 14a and 26a of the window members 14 and 26 provided on one end side and the other end side of the cell channel 4 respectively have a convex curved surface on the surface opposite to the cell channel 4. However, the present invention is not limited thereto, and is applicable to a case where the lens portions 14a and 26a have various lens shapes. For example, the lens portions 14a and 26a may have the convex curved surface on the cell channel 4 side or on both sides, may have a concave curved surface on at least one side, or may have a convex curved surface on one side and a concave curved surface on the other side. That is, in the present invention, the peripheral edge portions 14b and 26b whose both surfaces are flat are provided around the lens portions 14a and 26a, and pressing members formed from the resin packings 18 and 30 and the like may be in surface contact with the peripheral edge portions 14b and 26b.

In the embodiment described above, although the window members 14 and 26 have the same configuration, the window members 14 and 26 are not necessarily required to have the same configuration and may have different configurations.

The invention claimed is:

1. A flow cell comprising:
a housing including a cell channel in which a sample flows through, wherein the housing includes an opening which is communicating with the cell channel and is provided on at least one end side of the cell channel, and a flat surface at an edge of the opening;
a window member including a lens portion at a central portion and a peripheral edge portion, wherein a first surface and an opposite and parallel second surface of the peripheral edge portion of the window member are flat, and the first surface of the peripheral edge portion is provided facing the flat surface of the housing so as to seal the opening; and
a pressing member provided opposite to the cell channel with the window member interposed therebetween, wherein the pressing member has in the central portion a hole through which light passes, and wherein the pressing member is in surface contact with the second surface of the peripheral edge portion of the window member to press the window member toward the cell channel, and
wherein the first surface of the peripheral edge portion is in surface contact with the flat surface of the housing so as to seal the opening when the pressing member presses the second surface of the peripheral edge of the window member.

2. The flow cell according to claim 1, wherein the lens portion of the window member has a convex lens on a surface opposite to the cell channel.

3. The flow cell according to claim 2, wherein the convex lens has a lateral surface which is perpendicular to the first surface of the peripheral edge portion or forms an angle larger than 90 degrees with respect to the first surface of the peripheral edge portion.

4. The flow cell according to claim 1, wherein the peripheral edge portion of the window member has a light transmittance lower than that of the lens portion.

* * * * *